United States Patent [19]

Takamizawa et al.

[11] Patent Number: 4,644,214
[45] Date of Patent: Feb. 17, 1987

[54] PROBE FOR ELECTRONIC SCANNING TYPE ULTRASONIC DIAGNOSTIC APPARATUS

[75] Inventors: Kinya Takamizawa; Isao Uchiumi, both of Yokohama, Japan

[73] Assignee: Tokyo Shibaura Denki Kabushiki Kaisha, Kawasaki, Japan

[21] Appl. No.: 880,353

[22] Filed: Jun. 26, 1986

Related U.S. Application Data

[63] Continuation of Ser. No. 285,451, Jul. 21, 1981, abandoned, which is a continuation of Ser. No. 32,774, Apr. 24, 1979, abandoned.

[30] Foreign Application Priority Data

Apr. 25, 1978 [JP] Japan ................................ 53-48343

[51] Int. Cl.⁴ .......................................... H01L 41/08
[52] U.S. Cl. .................................. 310/334; 310/335; 310/317
[58] Field of Search ............. 310/317, 322, 334–337, 310/326, 327, 366, 367; 73/626; 128/660; 367/103, 138

[56] References Cited

U.S. PATENT DOCUMENTS

| | | | |
|---|---|---|---|
| 3,936,791 | 2/1976 | Kossoff | 310/335 X |
| 3,971,962 | 7/1976 | Green | 310/335 X |
| 4,058,003 | 11/1977 | Macovski | 310/335 X |
| 4,101,795 | 7/1978 | Fukumoto et al. | 310/336 |
| 4,145,931 | 3/1979 | Tancrell | 310/334 X |
| 4,152,678 | 5/1979 | Shott et al. | 310/334 X |
| 4,155,259 | 5/1979 | Engeler | 310/334 X |
| 4,161,122 | 7/1979 | Buchner | 310/334 X |
| 4,180,792 | 12/1979 | Lederman et al. | 310/334 X |

*Primary Examiner*—Mark O. Budd
*Attorney, Agent, or Firm*—Oblon, Fisher, Spivak, McClelland & Maier

[57] ABSTRACT

A probe for an electronic scanning type ultrasonic diagnostic apparatus in which a plurality of real transducers and one or more pseudo-transducers are arranged in a row on a supporting plate. In order to equalize the ultrasonic directivity characteristics of each of the real transducers, the pseudo-transducers are arranged adjacent to the real transducers which are located at the ends of the row, and have approximately the same shape and dimensions as the real transducers.

7 Claims, 9 Drawing Figures

PROBE FOR ELECTRONIC SCANNING TYPE ULTRASONIC DIAGNOSTIC APPARATUS

This application is a continuation of application Ser. No. 285,451, filed July 21, 1981 now abandoned, which is a continuation of application Ser. No. 032,774, Apr. 24, 1979, now abandoned.

BACKGROUND OF THE INVENTION

1. Field of the Invention

The present invention relates to a probe for electronic scanning type ultrasonic diagnostic apparatus.

2. Description of the Prior Art

In ordinary ultrasonic diagnostic apparatus, the electro-acoustic transducers comprise piezoelectric resonators which direct an ultrasonic pulse at the portion of a living body to be observed, and successively detect the ultrasonic pulse as it is reflected from the boundaries of the organs of the living body. By changing the direction of the ultrasonic pulse which is directed into the living body, two dimensional information concerning the structure of the organs of the living body is obtained and displayed on a CRT.

In order to easily obtain two dimensional information concerning the structure of each portion of the living body, the probe which houses the plurality of electro-acoustic transducers is normally separated from the diagnostic apparatus and is connected to the apparatus by an electric cable.

As described above, in such an ultrasonic diagnostic apparatus for scanning by ultrasonic waves, it is necessary to change successively both the transmission direction of ultrasonic pulses directed into the living body and the reception direction of reflected ultrasonic signals from the living body. Although such a scanning operation may be carried out by mechanically changing the orientation of a transducer, it may also be carried out by sequentially driving a plurality of transducers or by successively shifting a drive timing thereof. The ultrasonic diagnostic apparatus in which ultrasonic scanning is carried out by electronically controlling a plurality of transducers in this manner is called an electronic scanning type ultrasonic diagnostic apparatus.

There are two scanning types of electronic scanning type ultrasonic diagnostic apparatus. One is the linear scanning type and the other is the sector scanning type. In the linear scanning type, scanning is executed by changing over ultrasonic transducers by means of an electronic switch for transmission and reception of the ultrasonic wves, and in the sector scanning type, scanning is executed by changing an equiphase plane by means of a relative change of transmission and reception timings of the ultrasonic waves. In both of these types of apparatus, the ultrasonic probe in which a plurality of ultrasonic transducers are arranged in a row is essential. In a probe having such a structure, however, the ultrasonic directivities of the transducers which are near to the end of the row differ from those of the transducers which are near to the center of the row. This has an adverse effect on the ultrasonic scanning and gives rise to the problem that with an ultrasonic diagnostic apparatus using such an probe a high quality sectional image is not obtained.

Figure 1:
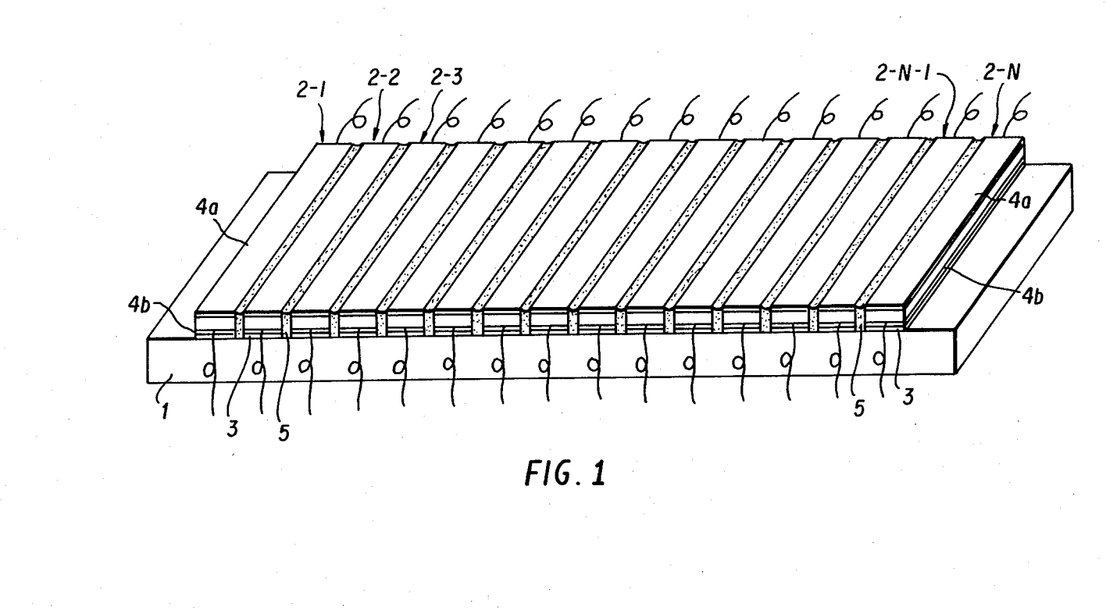
FIG. 1 is a perspective view showing the structure of a conventional probe for an ultrasonic diagnostic apparatus.

This problem will now be described in detail. FIG. 1 shows a cross sectional view of the conventional probe. On a supporting plate 1 which is an ultrasonic wave absorber, a plurality of ultrasonic transducers 2-1 to 2-N are arranged in a row and fixed by backing material 3. If the thickness oscillation of the transducers is to be utilized, each transducer is provided with electrodes 4a and 4b respectively on the upper and lower faces thereof. In these electrodes, each electrode 4a provided on the upper face of the transducer, is grounded, while high voltage pulses are applied to the electrode 4b, or electric signals corresponding to the reflected ultrasonic waves are extracted therefrom. Surfaces of the electrodes 4a are covered with a coating layer (not shown), for example with epoxy resin, in order to protect the electro-acoustic transducers 2-1 to 2-N and to obtain good and comfortable contact to a living body. In addition, spacer 5 made of an ultrasonic absorber may be inserted in between these transducers. In this way, the mutual influence between these transducers 2-1 to 2-N may be minimized. However, in fact, oscillations of each of the transducers 2-1 to 2-N still do affect oscillations of neighbouring transducers, due to the supporting plate 1, backing material 3, spacer 5 and coating layer etc. This influence is felt both in terms of mechanical interference and electrical impedence matching. While the structure of the device is made to neutralize these effects, still some influence remains. Consequently, when each of the transducers 2-1 to 2-N oscillates, it interferes with the other transducers.

Of the transducers which are arranged in a row, those transducers which are near to the center have generally similar ultrasonic directivities since they are arranged with approximately the same configuration and environment one each side thereof. Therefore, each of the transducers which is near to the center shows a symmetrical directivity. However, those transducers which are near to the end of the row, especially the transducers 2-1 and 2-N which are provided at the left and right ends, while having similar transducers on one side, have no transducer on the other side. These transducers therefore show ultrasonic directivities which are different from those of the transducers which are near to the center. Namely, each of the transducers 2-1 and 2-N shows an asymmetrical directivity. Such asymmetrical directivities of the transducers which are near to the end of the row exert a harmful influence as a whole upon the directivity characteristics for transmission and reception of ultrasonic waves. As a result, a sectional image of high quality can not be obtained in the case where the aforementioned probe is used in the ultrasonic diagnostic apparatus.

On the other hand, generally in the sector type ultrasonic diagnostic apparatus, all transducers are simultaneously used and the scanning is carried out by changing the drive timing of the transducers. Therefore the directivity characteristic of each transducer is desirably, as far as possible, non-directional. However, when the conventional probe in which the transducers arranged in a row is used, the directivity characteristics of the transducers which are near to the end of the row differ from those of the transducers which are near to the center, so the adverse effect on the image, described above, is particularly distinguished in the case of such a sector scanning type ultrasonic diagnostic apparatus.

In the probe in which a plurality of transducers are arranged in a row, it is known that an acoustic lens having a focusing effect can be provided on the transducers in order to sharpen the directivity characteristics at the plane intersecting the direction of the row. Such a construction is described in detail in U.S. Pat. No. 3,936,791. The probe having the acoustic lens is advantageous only for sharpening the directivity characteristics at the intersecting plane. However, even though a probe of this type is used, deterioration of image quality still appears, because the directivity characteristics of the transducers which are near to the end of the row are still asymmetrical.

BRIEF SUMMARY OF THE INVENTION

It is therefore one object of the present invention to provide a probe for an ultrasonic diagnostic apparatus in which all of the transducers have approximately the same directivity characteristics.

Another object of the present invention is to provide a probe with a focusing lens, in which all of the transducers have approximately the same directivity characteristics.

In one embodiment of the present invention, there is provided a probe for an ultrasonic diagnostic apparatus comprising a supporting plate, a plurality of electro-acoustic transducers arranged in a row on the supporting plate and one or more pseudo-transducers provided on the supporting plate adjacent to the end of the row of the transducers which are actually driven, where each pseudo-transducer has almost the same shape and dimensions as those of the actual transducers.

In another embodiment of the present invention, there is further provided one or more vibrator materials being wider than the pseudo-transducers and arranged on the supporting plate adjacent to the pseudo-transducers.

In a further embodiment of the present invention, there is provided a probe with an acoustic focusing lens for an ultrasonic diagnostic apparatus comprising, a supporting plate, a plurality of electro-acoustic transducers arranged in a row on the supporting plate, one or more pseudo-transducers arranged on the supporting plate adjacent to the end of the row and one or more vibrator materials arranged on the supporting plate adjacent to the pseudo-transducers, in which these vibrator materials ae wider than the transducers, and the lens is elongated over the vibrator materials.

According to the present invention, both transducers near to the end of the row and transducers near to the center of the row have practically the same directivity characteristics, that is, symmetrical directivity characteristics. Consequently, a sectional image of high quality can be obtained by using the probe of the present invention.

The present invention solves the problem of an asymmetrical directivity of the transducers which are near to the end of the row and thereby avoids deterioration of image quality.

Further objects and advantages of the present invention can be more fully understood from the following detailed description taken in conjunction with the accompanying drawings.

BRIEF DESCRIPTION OF THE DRAWINGS

FIG. 6 shows the structure of the probe of a further embodiment of the present invention.

DESCRIPTION OF THE PREFERRED EMBODIMENTS

Figure 2:
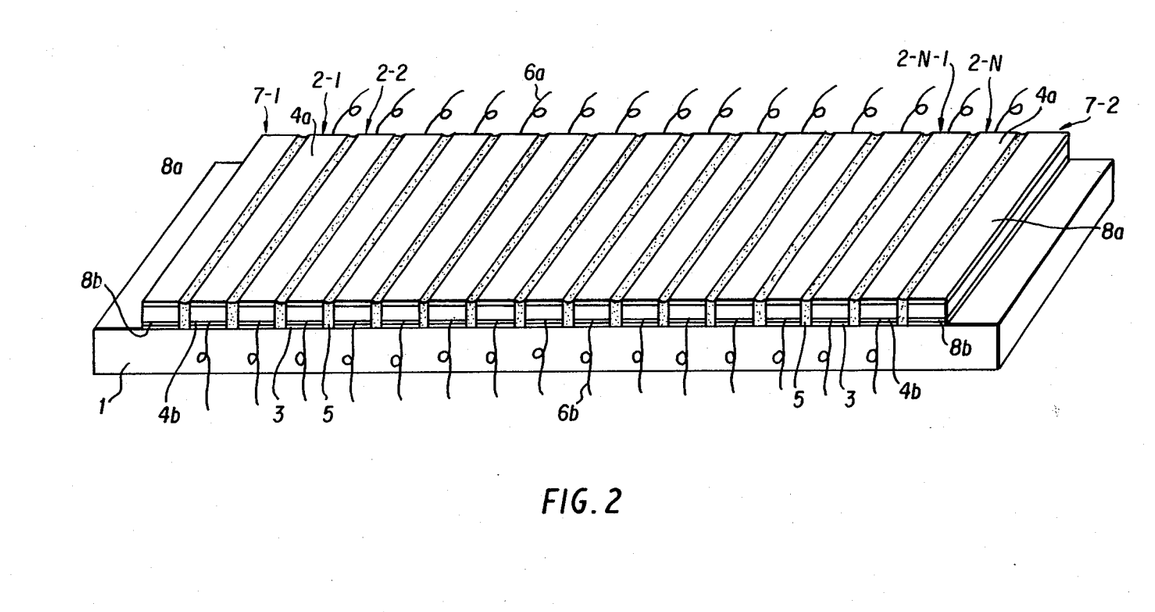
FIG. 2 is a perspective view showing the structure of a probe for an ultrasonic diagnostic apparatus of the present invention.

Referring now to FIG. 2 of the drawing, a plurality of transducers 2-1 to 2-N are arranged in a row on a supporting plate 1 which is constructed with an ultrasonic absorber. These transducers 2-1 to 2-N, which are at an equal interval from one another, are fixed on the supporting plate 1 by means of backing materials 3. In order to transmit and receive ultrasonic waves by using the thickness oscillation of the transducers, each transducer has electrodes 4a and 4b on the upper and lower faces thereof, and leads 6a and 6b are connected to the electrode 4a and 4b respectively.

Pseudo-transducers 7-1 and 7-2 are provided adjacent to the transducers 2-1 and 2-N which are at the ends of the row. Each of the pseudo-transducers 7-1 and 7-2 has almost the same shape and dimensions as those of the transducers 2-1 to 2-N, and the distance between the pseudo-transducer and the actual transducer is approximately the same as the separation between each of the transducers. A spacer 5 is inserted in between each pair of transducers. Each pseudo-transducer has electrodes 8a and 8b on the upper and lower faces thereof, and is fixed on the supporting plate 1 by means of a backing material 3 in the same manner as the transducers 2-1 to 2-N. A spacer 5 is also inserted between the transducer 2-1 and the pseudo-transducer 7-1, and the transducer 2-N and the pseudo-transducer 7-2, in the same manner as the transducers 2-1 to 2-N.

In the probe having above-mentioned structure, the transducers which are actually driven are the transducers 2-1 to 2-N. However, since the pseudo-transducers 7-1 to 7-2 are provided adjacent to the transducers existing near to the end of the row, these transducers, for example, transducers 2-1, 2-2, 2-N-1 and 2-N, have the same directivity characteristics as those of the transducers which are near to the center of the row. Namely, by providing the pseudo-transducers 7-1 and 7-2 adjacent to the end of the row, all of the transducers 2-1 to 2-N have symmetrical directivity characteristics.

Figure 3:
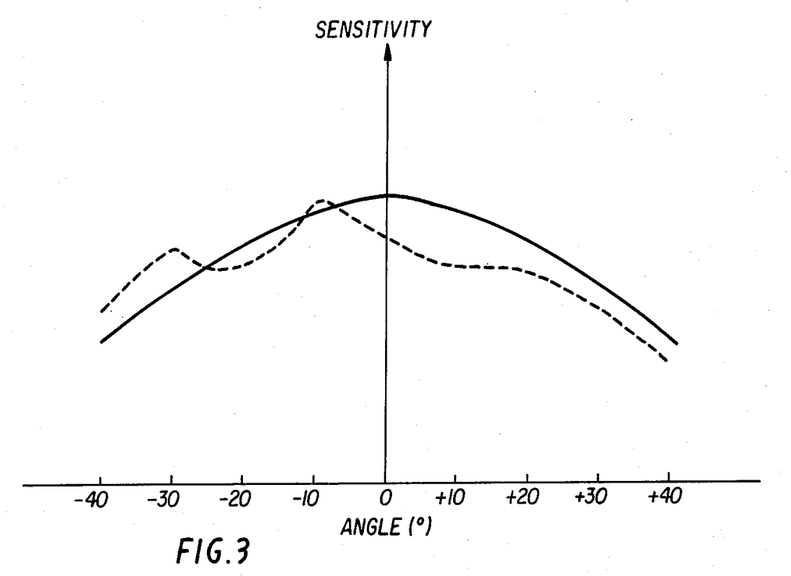
FIG. 3 shows directivity characteristics of the transducers which are near to the end of the row in the conventional probe and the probe of the present invention.

Referring now to FIG. 3, the broken line shows the directivity characteristics of the transducer 2-1 illustrated in FIG. 1, and the solid line shows the directivity characteristics of the transducer 2-1 in FIG. 2. In FIG. 3, the horizontal axis shows the angular displacement and the vertical axis shows the sensitivity. Further, this characteristic is obtained in the case where the width of both transducer and pseudo-transducer is approximately 0.4 mm and the frequency of ultrasonic waves is 2.4 MHz.

It can be readily seen from FIG. 3 that the transducer which is at the end of the row has a symmetrical directivity characteristic. Consequently a sectional image of high quality can be obtained when the probe having the structure shown in FIG. 2 is used for an electronic scanning type ultrasonic diagnostic apparatus, especially for a sector scanning type ultrasonic diagnostic apparatus.

In the above mentioned embodiment, only pseudo-transducers 7-1 and 7-2, each of which has the same shape and dimensions, are provided adjacent to the transducers 2-1 and 2-N, respectively. However, the present invention is not limited to this embodiment. Namely, vibrator materials which are wider than the pseudo-transducers can be further provided adjacent to the pseudo-transducers. Also, electrodes and leads can be provided on both pseudo-transducers and vibrator materials.

Figure 4:
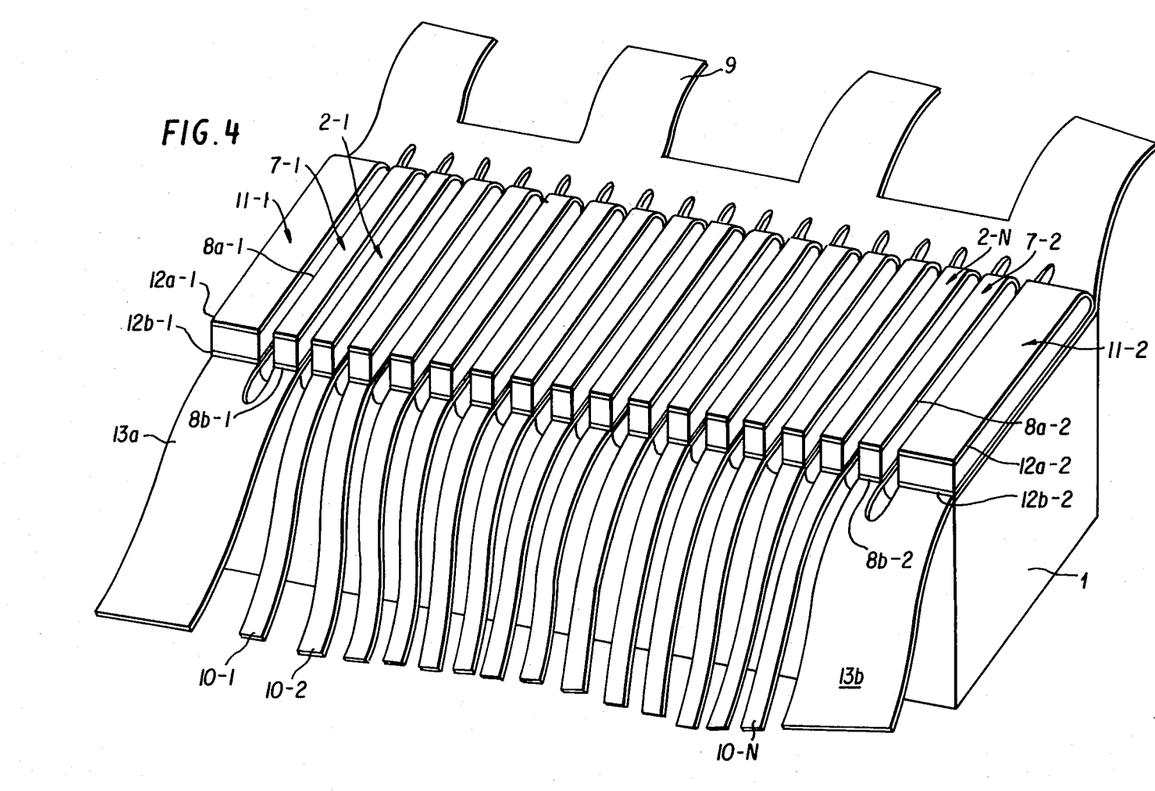
FIG. 4 is a perspective view showing the structure of the probe of another embodiment of the present invention.

Such an embodiment of the probe is shown in FIG. 4. On a supporting plate 1 made of an ultrasonic wave absorber, for example rubber-ferrite, a plurality of transducers 2-1 to 2-N are arranged in a row. Electrodes 4a and 4b are respectively provided on the upper and lower face thereof. In this embodiment, transducers 2-1 to 2-N are respectively made of piezoelectric ceramics, the spacing of each transducer is about 300μ, and the pitch is 370μ.

Electrodes 4a are respectively turned toward the lower face at the end of each transducer, and connected to a common lead 9. Further, electrodes 4b are connected to individual leads 10-1 to 10-N respectively.

Pseudo-transducers 7-1 and 7-2 and vibrator materials 11-1 and 11-2 are respectively arranged at the side of the transducers which are actually driven. Pseudo-transducers 7-1 and 7-2 have the same shape and dimensions, and the width of each of the vibrator materials 11-1 and 11-2 is wider than the pseudo-transducers. The pseudo-transducers 7-1 and 7-2 and the vibrator materials 11-1 and 11-2 are made of the same materials as the transducers 2-1 to 2-N. Electrodes 8a-1, 8a-2 and 8b-1, 8b-2 are respectively provided on the upper and lower face of the pseudo-transducers, and electrodes 12a-1, 12a-2 and 12b-1, 12b-2 are respectively provided on the upper and lower face of the vibrator materials.

Electrode 8a-1 and electrode 12a-1 are commonly connected to the common lead 9, while electrode 8b-1 and electrode 12b-1 are connected to each other by a lead 13a. Similarly, electrodes 8b-2 and 12b-2 are connected to each other by a lead 13b. The common lead 9, leads 10-1 to 10-N and leads 13a and 13b are made of a copper leaf of 50μ thickness.

Figure 7:
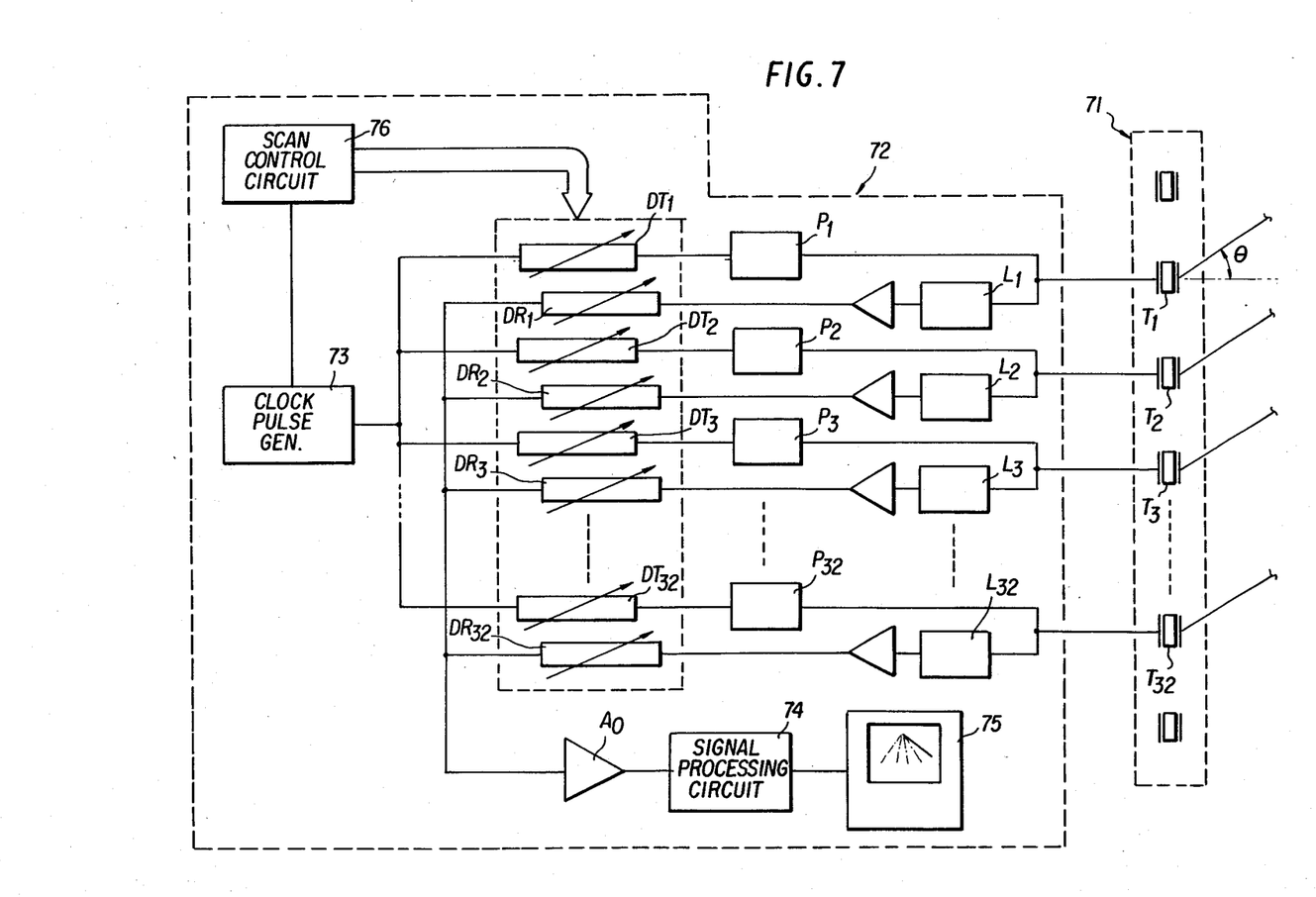
FIG. 7 is a block diagram of a sector scanning type ultrasonic diagnostic apparatus in which the probe of the present invention is incorporated.

While the common lead 9 and leads 13a and 13b are grounded, leads 10-1 to 10-N are respectively connected to pulsers and to limiters shown in FIG. 7. Therefore, high voltage pulses with different phases are applied to the respective transducers 2-1 to 2-N through leads 10-1 to 10-N, and as a result ultrasonic wave pulses are emitted in the prescribed direction. On the other hand, ultrasonic waves reflected from the living body are received by the transducers 2-1 to 2-N and are converted to electric signals in order to display the sectional image of the living body.

In such a manner, the transmitting and receiving operations are carried out by the transducers 2-1 to 2-N. Here, at both sides of the transducer 2-1, for example, the transducer 2-2 and the pseudo-transducer 7-1 are provided. Therefore the transducer 2-1 has the same surroundings as the transducers which are near to the center of the row. Consequently, the transducers which are at the end of the row and the other transducers which are near to the center of the row have approximately the same ultrasonic directivity characteristics.

The process for making the probe shown in FIG. 4 is described hereinafter. First of all, a supporting plate, a base vibrator material with electrode materials on both sides, a copper leaf having a predetermined pattern for a common lead 9, and a copper leaf having a predetermined pattern for leads 13a, 13b and 10-1 to 10-N are prepared. Then these copper leaves are put between the supporting plate and the base vibrator material and fixed by a backing material. Then, the base vibrator material is cut into a plurality of pieces separated electrically from each other. At this time, the transducers 2-1 to 2-N, the pseudo-transducers 7-1 and 7-2 and the vibrator materials 11-1 and 11-2 are formed by cutting the base vibrator material. This method has the advantage that the pseudo-transducers 7-1 and 7-2, the vibrator materials 11-1 and 11-2 and the transducers 2-1 to 2-N are simultaniously and easily made.

Figure 5A:
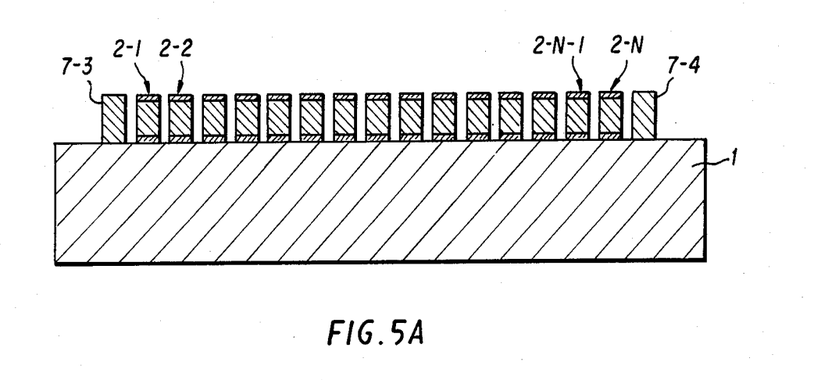
FIGS. 5A and 5B are cross sectional views of other embodiments of the probe of the present invention.
Figure 5B:
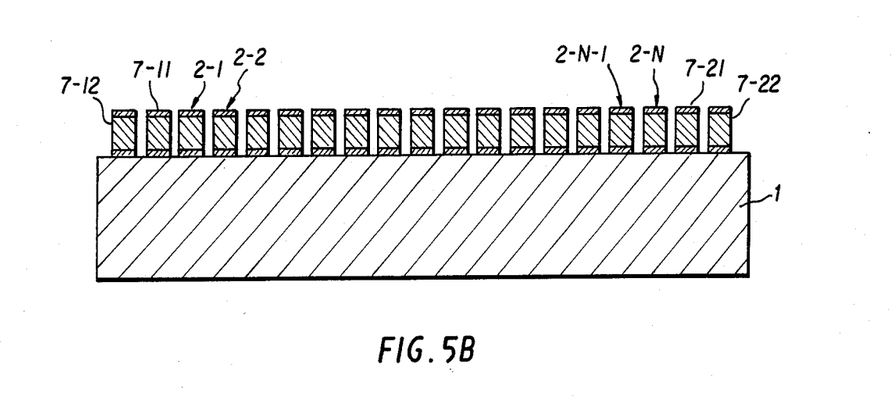

Although the pseudo-transducers 7-1 and 7-2 have electrodes as shown in FIG. 4, the present invention is not limited to this embodiment. FIG. 5 shows another embodiment of the present invention. In FIG. 5A, the pseudo-transducers 7-3 and 7-4 do not have electrodes. Furthermore, a plurality of pseudo-transducers can be arranged on both sides as shown in FIG. 5B. According to this embodiment, two pseudo-transducers 7-11 and 7-12 are arranged at one side and two pseudo-transducers 7-21 and 7-22 are arranged at the other side. Although the directivity characteristics of the probe rises as the number of the pseudo-transducer increases, it is sufficient to have only one pseudo-transducer for each side.

Figure 6A:
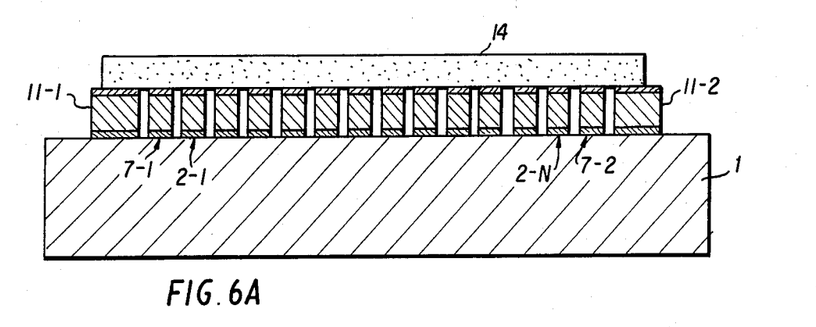
FIG. 6A is a horizontal cross sectional view and FIG. 6B a vertical cross sectional view.
Figure 6B:
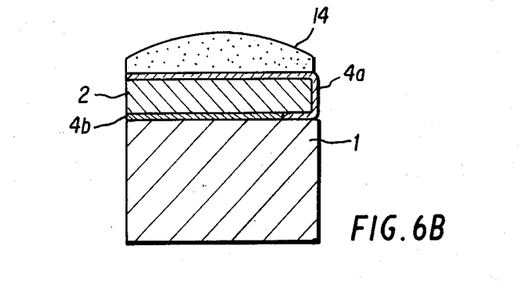

A further embodiment of the present invention is shown in FIGS. 6A and 6B. In this embodiment, transducers 2-1 to 2-N which are actually driven, pseudo-transducers 7-1 and 7-2 which have the same structure as the transducers 2-1 to 2-N, and vibrator materials 11-1 and 11-2 which are wider than the pseudo-transducers are arranged in a row on a supporting plate 1 which is made of an ultrasonic absorber. In addition, an acoustic lens 14 is fixed on the transducers 2-1 to 2-N, the pseudo-transducers 7-1 and 7-2 and the vibrator materials 11-1 and 11-2. The acoustic lens 14 is made of a convex-shaped silicon rubber, and it concentrates ultrasonic waves at the plane intersecting the direction of the row.

According to the present invention, the acoustic lens 14 extends from the vibrator materials 11-1 to 11-2. That is, the acoustic lens 14 covers not only the transducers 2-1 to 2-N, but also the pseudo-transducers 7-1 and 7-2 and the vibrator materials 11-1 and 11-2. Consequently, ultrasonic waves transmitted from the tranducers 2-1 and 2-N which are at the end of the row and ultrasonic waves received by these transducers are necessarily passed through the lens 14. As a result, a good directivity characteristic and concentration can be obtained. In this embodiment, a convex acoustic lens is used. However, a concave acoustic lens can be used in the case where the lens is formed by a material whose propagation velocity is faster than that in the living body.

FIG. 7 illustrates a sector scanning type ultrasonic diagnostic apparatus in which the probe of the present invention is used. The apparatus comprises an ultrasonic probe 71 and a diagnostic apparatus 72. Each of the embodiments shown in FIGS. 2, 4, 5 and 6 can be used as the probe 71. The diagnostic apparatus 72 is comprised of a clock pulse generator 73 which generates standard pulses, delay circuits DT1 to DT32 for producing the signals fed from the clock pulse generator 73 with a predetermined delay time, pulse generators P1 to P32 which are driven by the delay circuits DT1 to DT32 to deliver pulse signals of high voltage to electro-acoustic transducers T1 to T32, limiters L1 to L32 for limiting signals received by the transducers T1 to T32, amplifiers A1 to A32 for amplifying signals from the limiters L1 to L32, delay circuits DR1 to DR32 for producing the signals fed from the amplifiers A1 to A32 with a predetermined delay time, an amplifier A0 which amplifies the mixed signals of each of the output signals of the delay circuits DR1 to DR32, a signal processing circuit 74 for processing the output signals of the amplifier A0, a display 75 for displaying a sectional image of the living body in accordance with the output signals of the signal processing circuit 74 and a scan control circuit 76 for controlling the delay time of the delay circuits DT1 to DT32 and DR1 to DR32.

The direction of the ultrasonic pulses transmitted from the transducers T1 to T32 depends on the delay time given to the delay circuits DT1 to DT32. Namely, when the difference between the delay time of the i-th delay circuit DTi and that of the i-1-th delay circuit DTi-1 is $(d-c) \sin \theta$, ultrasonic waves transmitted from the transducers T1 to T32 tend to the direction of the aximuthal angle $\theta$, where d represents the center to center distance between two adjacent transducers, and c the sound velocity in the medium. Further, in order that the transducers receive the ultrasonic waves reflected from this direction, delays having the same time difference are given to the i-th delay circuit DRi and the i-1-th delay circuit DRi-1.

The operation of this apparatus will now be described. The scan control circuit 76 controls the scan so as to give a delay time in the amount of zero to the delay circuit DT32 and DR32, $(d/c) \sin \theta 1$ to the delay circuits DT31 and DR31, $2d/c \sin \theta 1$ to the delay circuits DT30 and DR30, and so forth. On the other hand, a first clock pulse generated from the clock pulse generator 73 is supplied to the pulse generators P1 to P32 through the delay circuits DT1 to DT32. As a result, high voltage pulses generated from the pulse generators are supplied to the corresponding transducers T1 to T32 respectively, and an ultrasonic beam is transmitted in the direction of $\theta 1$. Then the ultrasonic waves reflected from the living body are received by the transducers T1 to T32, and converted to an electric signal. At this moment, the converted electric signal is mixed through the limiters L1 to L32, the amplifiers A1 to A32 and the delay circuits DR1 to DR32. Therefore, the mixed electric signal represents an intensity of the ultrasonic waves reflected in the direction of $f1$. In such a manner, the mixed signal is again amplified by the amplifier A0, and processed by the signal processing circuit 74, and then supplied to the display 75.

Subsequently, the scan control circuit 76 controls the delay circuits DT1 to DT32 and DR1 to DR32 so as to transmit the ultrasonic beam from the transducers T1 to T32 in the direction of $\theta 2$. And the clock pulse generator 73 supplies a second clock pulse. Therefore, an electric signal corresponding to the reflected ultrasonic waves in the direction of $\theta 2$ is supplied to the display 75. In the same manner, the delay times are changed with every clock pulse generated from the clock pulse generator 73, scanning by the ultrasonic beams is carried out, and the sectional image of the living body is displayed as a result.

In the aforementioned embodiment, the probe of the present invention is incorporated in the sector scanning type ultrasonic diagnostic apparatus. However, it is apparent that the probe of the present invention can be incorporated in the linear scanning type ultrasonic diagnostic apparatus.

Obviously, numerous modifications and variations of the present invention are possible in light of the above teachings. It is therefore to be understood that within the scope of the claims, the invention may be practiced other than as specifically described herein.

What is claimed as new and desired to be secured by Letters Patent of the United States is:

1. A probe for an electronic scanning type ultrasonic diagnostic apparatus comprising:
   a supporting plate;
   a linear array of electro-accoustic transducers arranged in a row on said supporting plate and having equal intervals between consecutive transducers, each transducer having electrical connections for transmitting and receiving ultrasonic waves;
   a pair of electrically passive pseudo-transducers arranged on the supporting plate, with one pseudo-transducer at each end of the row of transducers, said pseudo-transducers being made of the same material and being of the same shape and dimensions as the transducers, the interval between the pseudo-transducer and the end transducer in the row being the same interval as between consecutive transducers in the row;
   whereby the ultrasonic directivity characteristics of the end transducers are made similar to those of the other transducers.

2. A probe for electronic scanning type ultrasonic diagnostic apparatus as claimed in claim 1, wherein each of the pseudo-transducers has a pair of electrodes.

3. A probe for electronic scanning type ultrasonic diagnostic apparatus as claimed in claim 2 or claim 1, wherein one or more electrically passive end pieces are provided adjacent to each of the pseudo-transducers, on the side thereof distant from the transducers, said end pieces being wider than the pseudo-transducers.

4. A probe for electronic scanning type ultrasonic diagnostic apparatus as claimed in claim 3, wherein each of the end pieces has a pair of electrodes.

5. A probe for electronic scanning type ultrasonic diagnostic apparatus as claimed in claim 2 or claim 1, wherein an acoustic lens for concentrating transmitting and receiving ultrasonic waves is superimposed on the transducers.

6. A probe for electronic scanning type ultrasonic diagnostic apparatus as claimed in claim 5, wherein the acoustic lens extends over both the transducers and the pseudo-transducers.

7. A probe for electronic scanning type ultrasonic diagnostic apparatus according to claim 3, wherein an acoustic lens for concentrating transmitting and receiving ultrasonic waves is superimposed on the transducers, the pseudo-transducers and the end pieces.

* * * * *